US008933409B2

(12) United States Patent
Siegel et al.

(10) Patent No.: US 8,933,409 B2
(45) Date of Patent: Jan. 13, 2015

(54) DEPTH-OF-INTERACTION IN AN IMAGING DEVICE

(75) Inventors: Stefan B. Siegel, Knoxville, TN (US); Robert A. Mintzer, Knoxville, TN (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 288 days.

(21) Appl. No.: 13/549,638

(22) Filed: Jul. 16, 2012

(65) Prior Publication Data

US 2013/0020487 A1 Jan. 24, 2013

Related U.S. Application Data

(60) Provisional application No. 61/509,606, filed on Jul. 20, 2011.

(51) Int. Cl.
*G01T 1/29* (2006.01)
(52) U.S. Cl.
CPC .................. *G01T 1/2985* (2013.01)
USPC .................................. 250/363.03

(58) Field of Classification Search
CPC ........................................ G01T 1/2985
USPC .................................. 250/363.03
See application file for complete search history.

(56) References Cited

FOREIGN PATENT DOCUMENTS

WO    WO 2013101956 A1 * 7/2013

OTHER PUBLICATIONS

Huini Du, "A Laboratory PET Scanner with Depth-of-Interaction Detectors for Mouse Studies and Molecular Imaging." [U. C. Davis dissertation, 2009] [retrieved Jun. 26, 2014 from <url:http://gradworks.uni.com/3358972.pdf>.*

* cited by examiner

*Primary Examiner* — Constantine Hannaher
(74) *Attorney, Agent, or Firm* — Peter Kendall (57) ABSTRACT

A method (70) of operation of a PET scanner (10) that determines the depth of interaction of the annihilation photons within the scintillator (32) in localizing a temporal photon pair along a line of response (LOR).

15 Claims, 5 Drawing Sheets

DEPTH-OF-INTERACTION IN AN IMAGING DEVICE

CROSS-REFERENCE TO RELATED APPLICATIONS

This application claims the benefit of U.S. Provisional Patent Application 61/509,606, filed on Jul. 20, 2011, the entire disclosure of which is hereby incorporated by reference.

FIELD OF THE INVENTION

This invention generally relates to imaging systems and, more particularly to, positron emission tomography (PET) scanners.

BACKGROUND OF THE INVENTION

Figure 1:
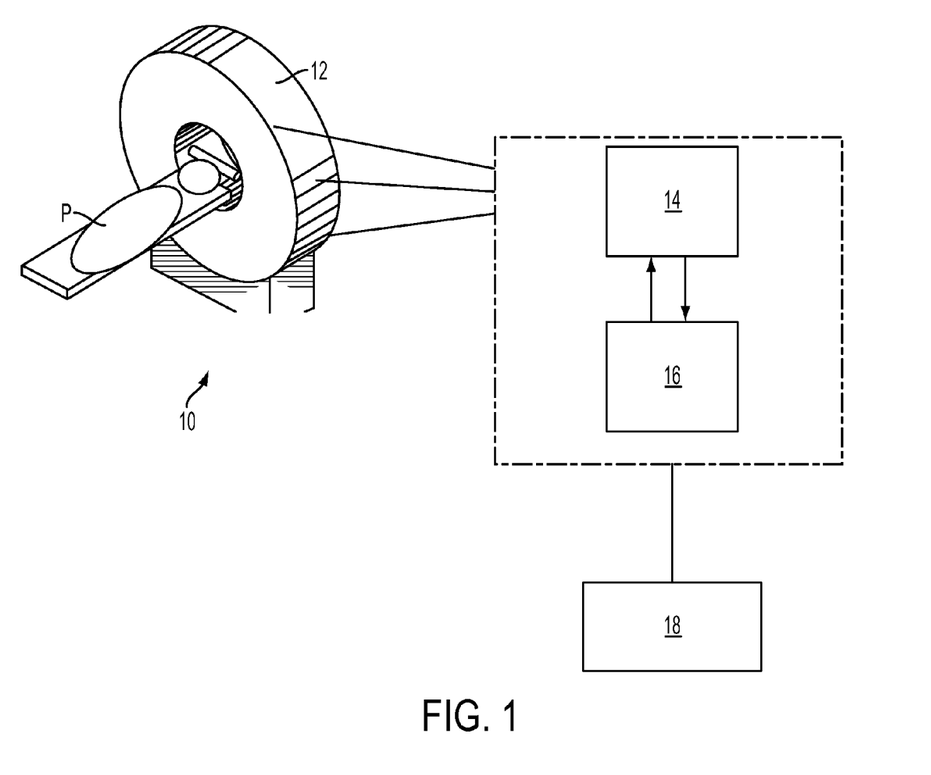
FIG. 1 is a block diagram of a PET system.

Positron emission tomography (PET), also known as PET imaging, is a type of nuclear medicine imaging that uses radioactive material, placed in a patient's body, to identify molecular activity and processes and, thus, assist in diagnosing disease, evaluating medical conditions, monitoring a patient's response to therapeutic interventions, etc. As shown in FIG. 1, a PET system 10 generally comprises an imaging device 12 that can detect radioactive emissions from the radioactive material (also known as radiopharmaceuticals or radiotracers) in the internal body area P under examination, a data processor 14 that analyzes the detected emissions information, and an image processor 16 (which in some configurations may be part of the data processor 14) that converts the processed data into image data or images of the area under examination via mathematical image reconstruction software. A user interface 18 (which typically includes an associated display such a touch screen display or non-touch screen display, keyboard and/or mouse) accompanies the processors 14, 16 and controls the operation of the system 10 and the various components. Although not shown in detail, the various components are operably connected to one another via appropriate control circuitry which is manipulated via the user interface 18.

Figure 2A:
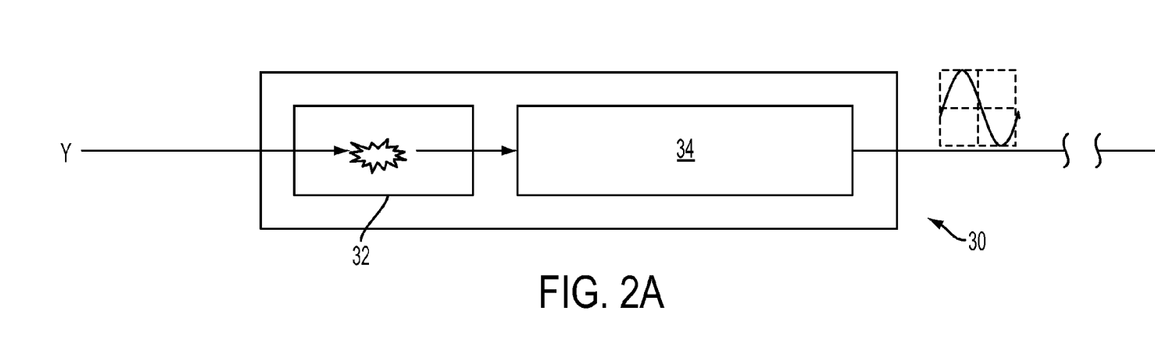
FIG. 2a is an illustration of a detector assembly for the PET system of FIG. 1.
Figure 2B:
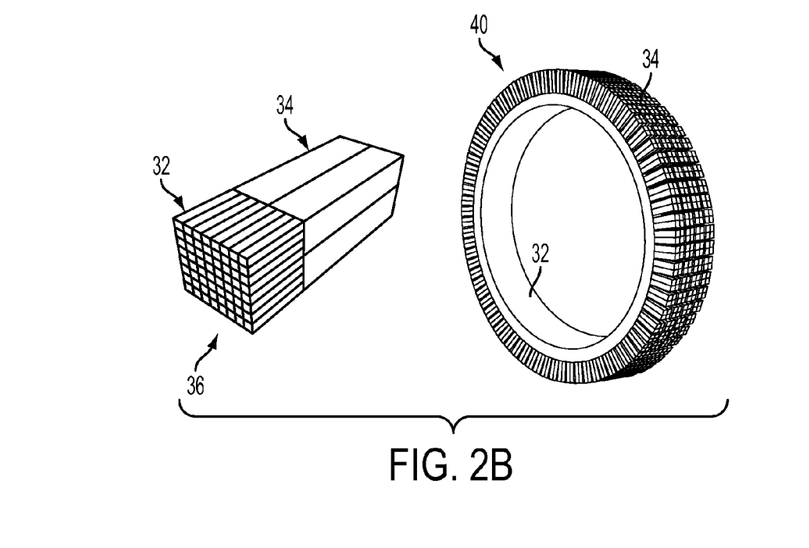
FIG. 2b is an illustration of a detector block and a detector ring, side by side, of the PET system of FIG. 1.

The imaging scanner 10 comprises a number of detector assemblies 30 of a scintillation crystal 32 optically coupled with a photosensor 34, for example, a photomultiplier tube (PMT) or avalanche photodiode (APD), that are arranged to form a series of concentric rings 40 (although other shapes, like hexagons or partial rings, may be formed). This is shown in FIGS. 2a and 2b. The detectors assemblies 30 (or scintillation detectors) are configured generally alike and may take on various coupling configurations, such as, one crystal 32 to one photosensor 34, a plurality of crystals 32 to one photosensor 34, or one crystal 32 to a plurality of photosensors 34. Both the crystals 32 and the photosensors 34 may be packed in modular structures and together in detector blocks 36. The scintillation detectors 30 are oriented in a respective detector ring 40 so the crystals 32 face the common central opening to form the inner diameter and the photosensors 34 are located behind the crystals 32 and form the outer diameter. The scintillation detectors 30 are further arranged in a respective ring 40 so that each has a diametrically opposed scintillation detector 30 across the central opening. The rings 40 are dimensioned so that the length of a patient's body P may be accommodated by the common central opening, in its axial direction (as shown in FIG. 1). Each detector ring 40 thus lies in a transverse plane of the patient's body P.

In operation, after an appropriate radiotracer is placed into a patient's body P and becomes concentrated in tissues of interest, the patient is placed in the central opening of the scanner 12. The radiotracer undergoes positron emission decay and each emitted positron travels in the tissue for a short distance until it interacts with an electron. The encounter annihilates both electron and positron, producing a pair of annihilation (gamma) photons γ moving in approximately opposite directions. The two photons γ travel to respective scintillation detectors 30 that are diametrically opposed within the detector ring 40. Each photon γ first enters and travels through the scintillation crystal 32 (the scintillator) which converts the high-energy photons into visible light (i.e., "optical light" or "optical photons"). The signal response of the scintillator 32 is typically a prompt intensity increase at the time of excitation followed by a decay with time. This is the scintillation process. The photosensor(s) 34 of the respective scintillation detector 30 detect the burst of light incident upon its coupling face(s) and, in turn, converts the light to an electrical signal.

All photons γ that interact with the detectors 30 are "registered" by the scanner 12 which forwards the electrical signals of registered events to the data processor 14. The data processor 14 analyzes the signals and determines if two registered events selected are a so-called coincidence event (i.e., a simultaneous or coincident detection of a photon pair). For this analysis, the data processor 14 utilizes only true coincidence events which occur when both photons γ of an annihilation event are detected by two opposing detectors 30 in coincidence within the resolving time of the scanner 12 (also known as the coincidence time-window), typically on the order of nanoseconds, and neither photon γ has undergone any form of interaction prior to detection. The source of a temporal photon pair then may be localized (via appropriate analysis) along the straight line that joins the two detectors 30 of the coincidence event (i.e., a line of coincidence or a line of response (LOR)).

Thousands of coincidence events are produced by each scan. Consequently, for each detector ring 40 (or transverse plane), a fan-beam of LORs over many angles by all the allowed coincident detector 30 pairs is produced. The large majority of coincidences are formed by diametrically-opposed detectors 30 in one ring 40 ("direct planes") and a smaller percentage of those coincidences are formed between adjacent planes ("cross planes"). The smaller/faster the resolving time of the detectors 30, the more precise the localization can be (e.g., a segment of a chord) and the better the signal-to-noise ratio (SNR) of the image, requiring fewer events to achieve the same image quality.

The data processor 14 forwards all coincidence data to the image processor 16 where final image data is produced via mathematical image reconstruction algorithms and software. Briefly, a map of the sources of each temporal photon pair may be constructed using the thousands of coincidence events and solving sets of simultaneous equations for the total activities along the LORs. The resulting map shows the tissues in which the radiotracer has become concentrated, and can be interpreted by an appropriate health professional.

In any imaging system, such as a PET system 10, knowing the depth-of-interaction (DOI), i.e. the depth within the detector 30 the signal of interest interacted, improves the accuracy in determining the direction from which the signal originated. Knowing the DOI also permits correction of event timing information, i.e. when the signal of interest interacted within the detector 30. For a PET scanner 12, knowing the DOI improves the image resolution and the system timing. As noted above, an improvement in system timing yields improved SNR in the tomographic images, particularly in time-of-flight (TOF) systems. Knowing the DOI can also improve energy resolution if there are depth-dependent losses of signal intensity which also aids in improving final image quality.

There is much interest in DOI determination for scintillation detectors 30 and there are many proposed methods in the medical literature. These proposed methods include, for example:

- using layers of dissimilar materials, such as scintillators of differing decay time, light yield efficiency, or wavelength to identify the layer of interaction;
- using weighted light-sharing across boundaries orthogonal to the DOI sought, such that the projected 2D image (flood image, position profile) is distorted by the shared light as a function of DOI;
- using photosensors at opposite ends of a scintillator and measuring the relative light intensity;
- measuring the spread of the light, and mapping that to the DOI; and
- placing multiple layers of thin detectors, either intrinsic or scintillation with an associated photosensor.

However, these proposed methods suffer from complexity and cost, and introduce degradations in other PET system performance criteria, such as sensitivity, energy resolution and, often, timing. Hence, they are only seen in academic prototypes and commercial animal imaging systems.

In scintillation detectors 30, the optical light is isotropically generated and there are usually a limited number of coupling or sensor surfaces of the photosensor(s) 34 by which the light is detected. In order to get a reasonable estimate of the energy deposited within the scintillator 32, reflectors are placed on all non-sensing surfaces of the photosensor(s) 34. The fact that the light undergoes multiple and varied reflections, dependent on the location of the energy deposition, means that there will be an associated shape to the response signal (typically, energy distribution versus photon count rate) from the photosensor(s) 34 which is superimposed on the scintillation light's intrinsic decay time. Advantageously, this shape may be exploited to yield an estimate of the DOI.

SUMMARY OF THE INVENTION

An embodiment of the present invention obviates the above problems by providing a method of determining the position of annihilation photon pairs along a line of response in a PET scanner, comprising the steps of: capturing annihilation photons by a scintillator of the scanner; converting, by the scintillator, the captured annihilation photons into optical photons; collecting the optical photons by a photosensor of the scanner, each photon having a respective arrival time to the photosensor; producing an electrical signal at the photosensor output for collected photons; and determining the depth of interaction of the annihilation photons within the scintillator by evaluating the differences in the optical photon path lengths within the scintillator and the optical photon arrival times to the photosensor. The determining step may further comprise evaluating the photosensor output signal shape. Also the photosensor output signal may describe optical photon arrival times and the determining step may further comprise evaluating the distribution of the optical photon arrival times to the photosensor. Also, the determining step may further comprise determining the accumulation rate of the collected photons. Also, the determining step may further comprise flagging when all the optical photons from the converting step have been collected and determining the accumulation rate of the collected photons.

Also, the determining step may comprise estimating the optical photon arrival times for collection. In such case, the estimating step may comprise a) estimating that the photons after capture heading directly towards the scintillator exit to the photosensor take at least $T_D=(n/c)*L_D$ time to exit, and b) estimating that the photons after capture that are directed away from the scintillator exit and then reflected back take at least $T_R=(n/c)*(2*L-L_D)$ time to exit, where n is the index of refraction of the scintillator; c is the speed of light in a vacuum; L represents the length of the scintillator from the capture entrance to the exit to the photosensor; $L_D$ represents the shortest distance between the depth of interaction and the scintillator exit; $T_D$ represents the expected time for light collection for the shortest distance between the depth of interaction and the exit to the photosensor, $L_D$; and $T_R$ represents the expected time for light collection for the reflection travel distance between the depth of interaction and the exit to the photosensor. Alternatively, the estimating step may comprise a) estimating that all of the optical photons are collected in $(n/c)*L$ time, for a case where the depth of interaction is near the scintillator capture entrance, b) estimating that half of the optical photons are collected in $(n/c)*L/2$ time and all of the optical photons are collected in $(n/c)*L*3/2$ time, for a case where the depth of interaction is at the scintillator center; and c) estimating that half of the optical photons are collected immediately and all of the optical photons are collected in $(n/c)*2*L$ time, for a case where the depth of interaction is near the scintillator exit, where n is the index of refraction of the scintillator, c is the speed of light in a vacuum, and L represents the length of the scintillator from the capture entrance to the exit to the photosensor.

An embodiment of the present invention also provides a method of localizing a temporal photon pair along a line of response in a molecular imaging scanner, comprising the steps of converting each annihilation photon detected by the scanner into a respective optical photon; converting the optical photons into respective electrical signals; sampling the electrical signal for each annihilation photon from a true coincidence event; and determining from the sampling the depth of interaction with the scanner of each annihilation photon from a true coincidence event. The determining step may comprise analyzing the shape of the sampled electrical signal. Also, the determining step may comprise analyzing the distribution of the optical photon arrival times within the scanner. Also, the photon arrival times within the scanner may derive from the electrical signals and the determining step may further comprise analyzing the distribution of the optical photon arrival times within the scanner. Also, the determining step may further comprise determining the accumulation rate of the optical photons by the scanner.

An embodiment of the present invention may also provide a PET scanner, comprising a scintillator that captures high energy photons from annihilation events and converts the high energy photons into optical photons, said optical photons adapted to form respective optical photon path lengths during scintillator operation; a photosensor, optically coupled to the scintillator, that collects the optical photons from the scintillator and produces respective electrical signals, each of said optical photons having a respective arrival time to the photosensor; and a data processor, operably connected to the scintillator and the photosensor, that determines the depth of interaction of the annihilation photons within the scintillator by evaluating the differences in the optical photon path lengths within the scintillator and the optical photon arrival times to the photosensor. The data processor may analyze the distribution of the optical photon arrival times to the photosensor. Also, the optical photon arrival times to the photosensor may derive from the electrical signals and the data processor may analyze the distribution of the optical photon arrival times to the photosensor. Also, the data processor may estimate the photon arrival times for collection. In such case, the data processor may analyze the distribution of the photon arrival times to the photosensor.

BRIEF DESCRIPTION OF THE DRAWINGS

For a better understanding of the present invention, reference is made to the following description of exemplary embodiments thereof, and to the accompanying drawings, wherein.

DETAILED DESCRIPTION

Figure 3:
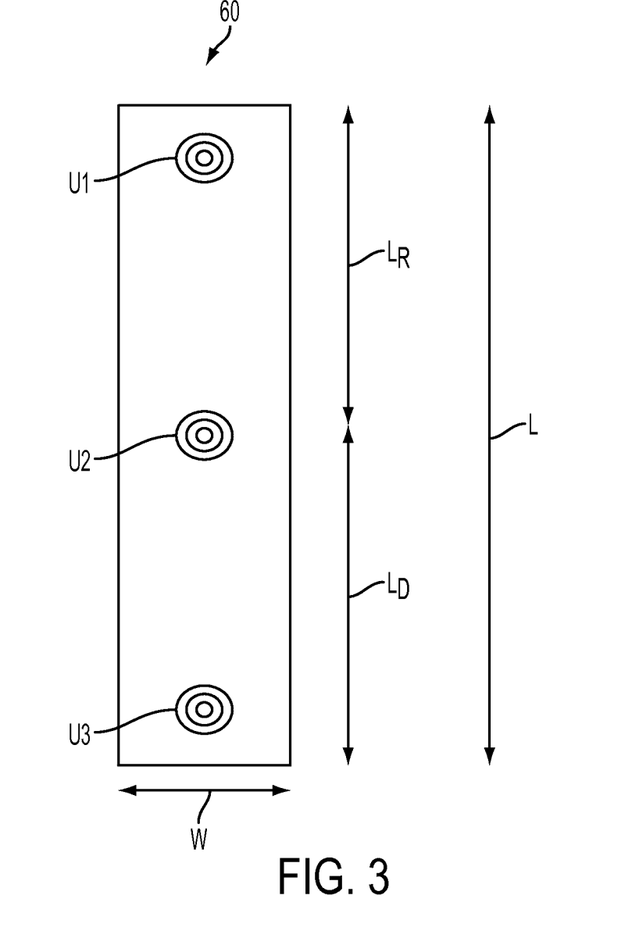
FIG. 3 is an illustration of a scintillator for a PET system to show the operation of a method carried out according to an embodiment of the present invention.

FIG. 3 is an illustration of a scintillator 60 for a PET system to show the operation of a method carried out according to an embodiment of the present invention. The scintillator 60 may be formed from any appropriate scintillation crystal, such as LSO, LYSO, BGO, etc. The scintillator 60 has a length L, a width W, an index of refraction n (not shown), and three representative depths of interaction (DOIs): U1 near the top, U2 at the center and U3 at the bottom, or exit, of the scintillator 60. Typical values for an LSO-based scintillator 60 of some of these parameters may be L=20 mm, W=4 mm, n=1.82. The speed of light c in a vacuum is 0.30 mm/ps, so the ratio of the index of refraction to the speed of light (n/c) is 6.07 ps/mm.

The shortest distance between an actual DOI and the top of the scintillator 60 from which the light must reflect to be detected is represented by a double-headed arrow $L_R$. The shortest distance between the actual DOI and the exit to the photosensor (not shown) is represented by a double-headed arrow $L_D$. Note that an end of both double-headed arrows $L_R$, $L_D$ meet at the representative central DOI U2 for illustration purposes only and the actual DOI may be along the length L of the scintillator 60 at any other representative DOI or, in fact, any distance from the top of the scintillator 60.

Figure 4:
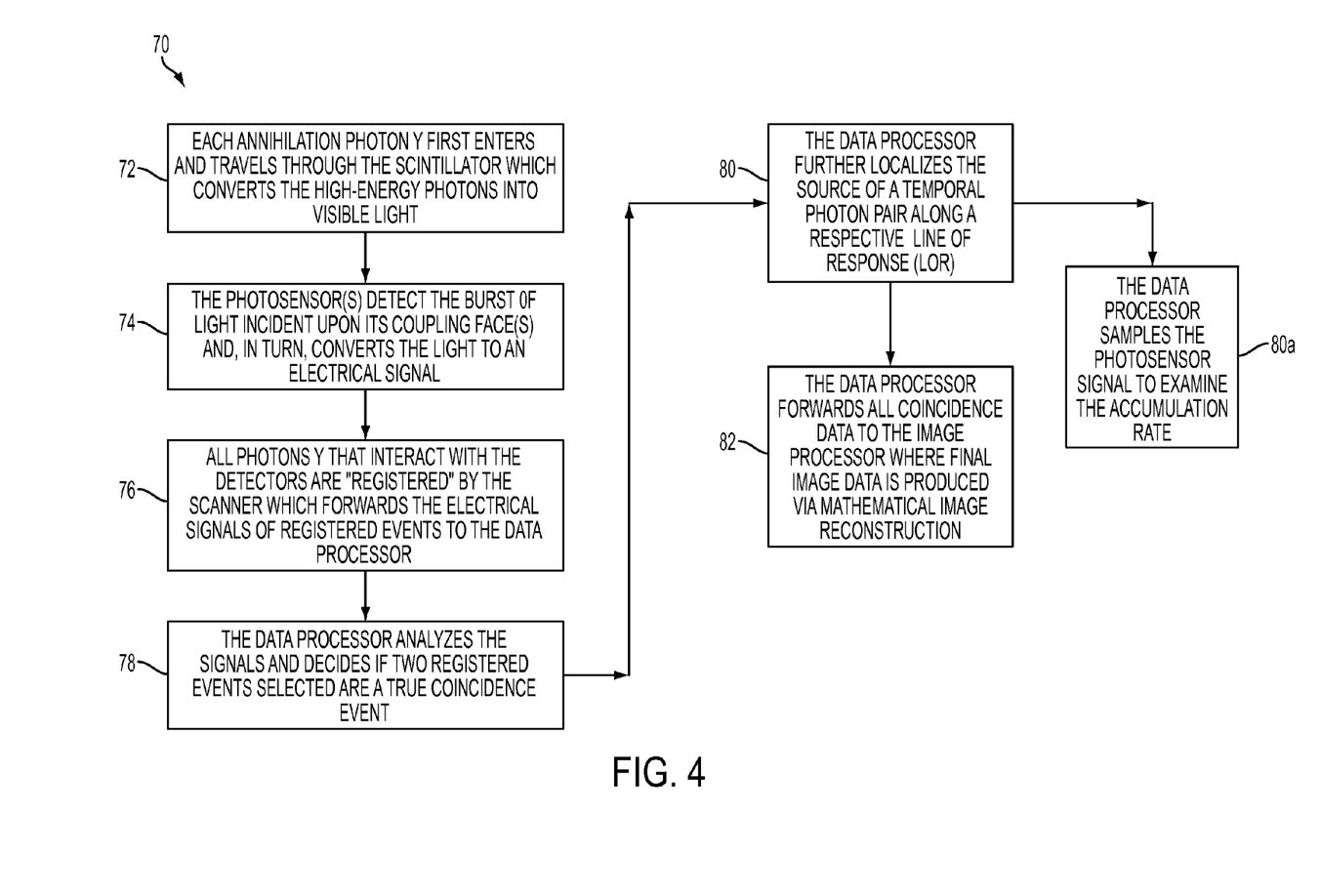
FIG. 4 is a block diagram of a method carried out according to an embodiment of the present invention.

FIG. 4 is a block diagram of a method 70 performed by the PET system 10 according to an embodiment the present invention. As noted previously, the radiotracer placed into a patient's body P undergoes positron emission decay and each emitted positron travels in the body's tissue until it interacts with an electron. The annihilation encounter produces a pair of annihilation (gamma) photons γ moving in approximately opposite directions. The two photons γ travel to respective scintillation detectors 30 that are diametrically opposed within the detector ring 40. Each photon γ first enters and travels through the scintillator 32 which converts the high-energy photons into visible light (Step 72). The photosensor(s) 34 detect the burst of light incident upon its coupling face(s) and, in turn, converts the light to an electrical signal (Step 74).

All photons γ that interact with the detectors 30 are "registered" by the scanner 12 which forwards the electrical signals of registered events to the data processor 14 (Step 76). The data processor 14 analyzes the signals and decides if two registered events selected are a true coincidence event (Step 78). The data processor 14 further localizes the source of a temporal photon pair along a respective line of response (LOR) (Step 80). The data processor 14 forwards all coincidence data to the image processor 16 where final image data is produced via mathematical image reconstruction algorithms and software (Step 82).

As part of analyzing the photosensor signals and localizing the source of the temporal photon pair, the data processor 14 samples the photosensor signal to examine the photon accumulation rate (Step 80a). Factoring in dispersion and the scintillation process, one can then use a low threshold to initiate sampling of the photosensor signal to look at the accumulation rate. This sampling can be done by means of analog processing, digital processing, or a combination of the two. With continuous sampling, the determination of the accumulation rate could be done retrospectively once some other mechanism, such as a discriminator, flags that all the light from an event has been captured.

The data processor 14 uses calculated expected times for light collection in the sampling. Light that enters the scintillator 60 and heads directly towards the exit of the scintillator 60 will take at least time $T_D=(n/c)*L_D$ to exit. The time $T_D$ therefore represents the expected time for light collection for the shortest distance between the actual DOI and the exit to the photosensor, $L_D$. Light that enters the scintillator 60 which is directed away from the exit will have to be reflected back and will take at least time $T_R=(n/c)*(2*L-L_D)$ to exit. The time $T_R$ therefore represents the expected time for light collection for the reflection travel distance between the actual DOI and the exit to the photosensor. The $T_R-T_D$ time difference is then $2*(n/c)*(L-L_D)$. Ignoring the scintillation light's intrinsic decay time and any losses due to absorption, for a case where the DOI is near the top of the scintillator 60 ($L_D \rightarrow L$), all of the light will be collected in $(n/c)*L$ time. For a case, where the DOI is at the center of the scintillator 60 ($L_D \rightarrow L/2$), half of the light will be collected in $(n/c)*L/2$ time and all of the light will be collected in $(n/c)*L*3/2$ time. For a case where the DOI is near the bottom of the scintillator 60 ($L_R \rightarrow L$), half of the light will be collected immediately and all of the light will be collected in $(n/c)*2*L$ time.

Figure 5A:
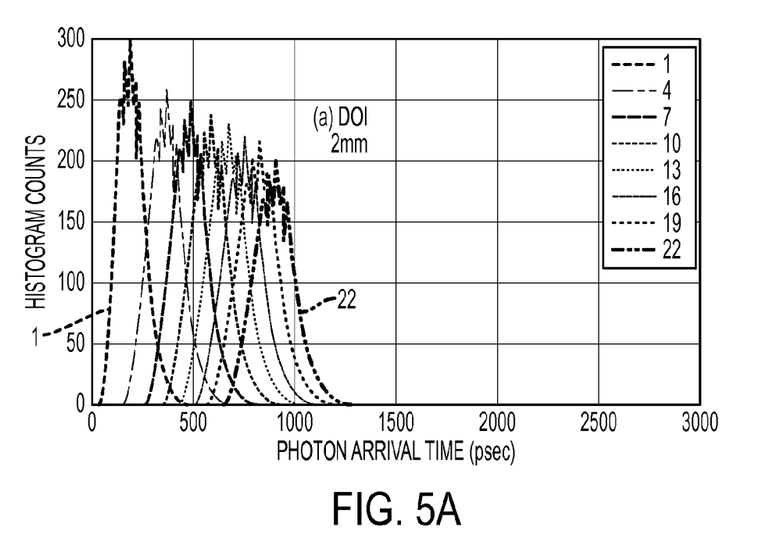
FIGS. 5a and 5b are exemplary plots of photon arrival time dispersion as a function of the number of photons waiting to arrive.
Figure 5B:
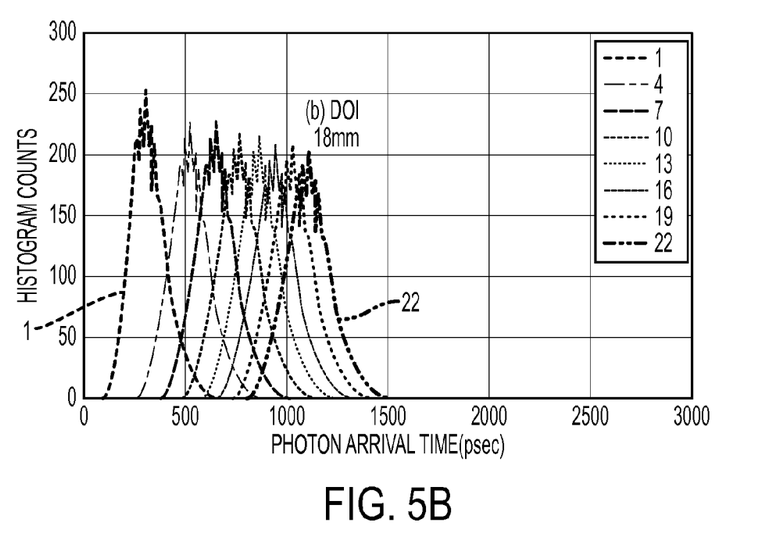

Note that simulations bear out some of the expected times for light collection from pixels (i.e., each scintillator crystal). An example would be the plots shown in FIGS. 5a and 5b. Specifically, FIG. 5a shows a plot of photon arrival time dispersion as a function of the number of photons arriving for a DOI of 2 mm away from the photosensor. FIG. 5b shows a plot of photon arrival time dispersion as a function of the number of photons arriving for a DOI of 18 mm away from the photosensor.

One can use time-based sampling of the photosensor signals, since the signals may be integrated, to take advantage of the spread and delay in accumulating various fractions of the photons, as illustrated in FIGS. 5a and 5b. This can be done by analog integration, continuous digital sampling of the varying waveform, or digitally on a device such as a digital silicon photomultiplier (SiPM), where the rate of cell triggering will follow the scintillation light distribution in time.

Advantageously, the method 70 of an embodiment of the present invention uses the inherent distribution/shape of the collected scintillation light in order to determine or estimate the DOI. Also, the method 70 exploits depth-dependent differences in optical photon path lengths within a scintillator (and thus the coupled photosensor arrival time) to estimate the DOI within the scintillator by an analysis of the photosensor output signal shape or other evaluation of the distribution of the optical photon arrival times. The method 70 may be adapted to provide a simple separation of the scintillator 60 into top-half/bottom-half for a determination of the DOI; however, there is a direct correlation between the resolution of the DOI determination and the extent of the scintillator separation. The method 70 may also take advantage of the fact that increasing the optical isolation of scintillating pixels drives the bulk of the light collected to be from direct photosensor illumination and light reflected from the surface opposite that of the photosensor coupling face. Such optical isolation may be accomplished by various known means, e.g., isolation structures in the photosensor array.

Other modifications are possible within the scope of the invention. For example, the subject patient to be scanned may be a human subject, animal subject or any other suitable object. Also, although the steps of the method 70 have been described in a specific sequence, the order of the steps may be re-ordered in part or in whole and the steps may be modified, supplemented, or omitted as appropriate. Also, the method 70 may use various well known algorithms and software applications to implement the steps and substeps. Further, the method 70 may be implemented in a variety of algorithms and software applications. Further, the method 70 may be supplemented by additional steps or techniques. It is also understood that the method 70 may carry out all or any of the steps using real-time data, stored data from a data archive or database, data from a remote computer network, or a mix of data sources.

Also, the various described instrumentation and tools are conventional and well known. They may be configured and interconnected in various ways as necessary or as desired. Further, although in the described method 70 the user may use self-contained instrumentation and tools, the user may use other instrumentation or tools in combination with or in place of the instrumentation and tools described for any step or all the steps of the method 70, including those that may be made available via telecommunication means. Further, the described method 70, or any steps, may be carried out automatically by appropriate instrumentation and tools or with some manual intervention.

What is claimed is:

1. A method of determining the position of annihilation photon pairs along a line of response in a PET scanner, comprising the steps of:
   a capturing annihilation photons by a scintillator of the scanner;
   b converting, by the scintillator, the captured annihilation photons into optical photons;
   c collecting the optical photons by a photosensor of the scanner, each photon having a respective arrival time to the photosensor;
   d producing an electrical signal at the photosensor output for collected photons; and
   e determining the depth of interaction of the annihilation photons within the scintillator by evaluating the differences in the optical photon path lengths within the scintillator and the optical photon arrival times to the photosensor,
   wherein the determining step further comprises determining an accumulation rate of the collected photons.

2. The method of claim 1, wherein the determining step further comprises evaluating the photosensor output signal shape.

3. The method of claim 1, wherein a photosensor output signal describes optical photon arrival times and the determining step further comprises evaluating the distribution of the optical photon arrival times to the photosensor.

4. The method of claim 1, wherein the determining step further comprises flagging when all the optical photons from the converting step have been collected and determining an accumulation rate of the collected photons.

5. The method of claim 1, wherein the determining step comprises estimating the optical photon arrival times for collection.

6. The method of claim 5, wherein the estimating step comprises a) estimating that the photons after capture heading directly towards a scintillator exit to the photosensor take at least $T_D=(n/c)*L_D$ time to exit, and b) estimating that the photons after capture that are directed away from the scintillator exit and then reflected back take at least $T_R=(n/C)*(2*L-L_D)$ time to exit, where n is an index of refraction of the scintillator; c is a speed of light in a vacuum; L represents a length of the scintillator from the capture entrance to the exit to the photosensor; $L_D$ represents a shortest distance between the depth of interaction and the scintillator exit; $T_D$ represents an expected time for light collection for the shortest distance between the depth of interaction and the exit to the photosensor, $L_D$; and $T_R$ represents the expected time for light collection for the reflection travel distance between the depth of interaction and the exit to the photosensor.

7. The method of claim 5, wherein the estimating step comprises a) estimating that all of the optical photons are collected in $(n/c)*L$ time, for a case where the depth of interaction is near the scintillator capture entrance, b) estimating that half of the optical photons are collected in $(n/c)*L/2$ time and all of the optical photons are collected in $(n/c)*L*3/2$ time, for a case where the depth of interaction is at a scintillator center; and c) estimating that half of the optical photons are collected immediately and all of the optical photons are collected in $(n/c)*2*L$ time, for a case where the depth of interaction is near a scintillator exit, where n is an index of refraction of the scintillator; c is a speed of light in a vacuum; and L represents a length of the scintillator from a capture entrance to the exit to the photosensor.

8. A method of localizing a temporal photon pair along a line of response in a molecular imaging scanner, comprising the steps of:
   a converting each annihilation photon detected by the scanner into a respective optical photon;
   b converting the optical photons into respective electrical signals;
   c sampling the electrical signal for each annihilation photon from a true coincidence event;
   d determining from the sampling the depth of interaction with the scanner of each annihilation photon from a true coincidence event,
   e wherein the determining step comprises analyzing the shape of the sampled electrical signal and;
   f comprising superimposing the shape of the electrical signal onto a shape of the Depth of Interaction.

9. The method of claim 8, wherein the determining step comprises analyzing a distribution of an optical photon arrival times within the scanner.

10. The method of claim 8, wherein photon arrival times within the scanner derive from the electrical signals and the determining step further comprises analyzing the distribution of optical photon arrival times within the scanner.

11. The method of claim 8, wherein the determining step further comprises determining an accumulation rate of the optical photons by the scanner.

12. A PET scanner, comprising:
a a scintillator that captures high energy photons from annihilation events and converts the high energy photons into optical photons, said optical photons adapted to form respective optical photon path lengths during scintillator operation;
b a photosensor, optically coupled to the scintillator, that collects the optical photons from the scintillator and produces respective electrical signals, each of said optical photons having a respective arrival time to the photosensor; and
c a data processor, operably connected to the scintillator and the photosensor, that determines a depth of interaction of the annihilation photons within the scintillator by evaluating differences in the optical photon path lengths within the scintillator and the optical photon arrival times to the photosensor, wherein the data processor analyzes a distribution of optical photon arrival times to the photosensor.

13. The method of claim 12, wherein the optical photon arrival times to the photosensor derive from the electrical signals and the data processor analyzes a distribution of optical photon arrival times to the photosensor.

14. The scanner of claim 12, wherein the data processor estimates photon arrival times for collection.

15. The scanner of claim 14, wherein the data processor analyzes a distribution of the photon arrival times to the photosensor.

* * * * *